(12) United States Patent
Eiteneer et al.

(10) Patent No.: US 7,383,745 B2
(45) Date of Patent: Jun. 10, 2008

(54) HEATED SAMPLING HOSE ASSEMBLY AND RELATED METHOD

(75) Inventors: Boris Nikolaevich Eiteneer, Aliso Viejo, CA (US); Glenn Charles England, Monarch Beach, CA (US); Brian Clifton Jacobs, Wildomar, CA (US)

(73) Assignee: General Electric Company, Schenectady, NY (US)

( * ) Notice: Subject to any disclaimer, the term of this patent is extended or adjusted under 35 U.S.C. 154(b) by 332 days.

(21) Appl. No.: 11/107,968

(22) Filed: Apr. 18, 2005

(65) Prior Publication Data

US 2006/0230845 A1 Oct. 19, 2006

(51) Int. Cl.
*G01N 1/00* (2006.01)
(52) U.S. Cl. .................................... 73/863.12
(58) Field of Classification Search ............ 73/863.11, 73/863.12
See application file for complete search history.

(56) References Cited

U.S. PATENT DOCUMENTS

| | | | |
|---|---|---|---|
| 3,696,247 A * | 10/1972 | McIntosh et al. ...... | 250/339.07 |
| 3,938,377 A | 2/1976 | Converse, III et al. | |
| 4,058,975 A | 11/1977 | Gilbert et al. | |
| 4,148,211 A * | 4/1979 | Sawa et al. ................ | 73/23.31 |
| 4,215,412 A | 7/1980 | Bernier et al. | |
| 4,283,947 A * | 8/1981 | George et al. ........... | 73/863.11 |
| 4,344,917 A * | 8/1982 | Schorno ...................... | 422/78 |
| 4,756,200 A * | 7/1988 | Ramsner et al. ......... | 73/863.11 |
| 4,958,529 A * | 9/1990 | Vestal ..................... | 73/864.81 |
| 5,336,390 A * | 8/1994 | Busack et al. ............. | 204/431 |
| 5,400,665 A * | 3/1995 | Zhu et al. ................. | 73/863.12 |
| 6,076,392 A | 6/2000 | Drzewiecki | |
| 6,145,545 A * | 11/2000 | Hartnagel et al. .......... | 138/113 |
| 6,305,407 B1 * | 10/2001 | Selby ......................... | 137/312 |
| 6,517,241 B1 | 2/2003 | Sanderson | |
| 6,528,018 B1 * | 3/2003 | Berndt ....................... | 422/70 |
| 6,565,255 B2 | 5/2003 | Sanderson | |
| 6,736,883 B2 * | 5/2004 | Sjostrom et al. ............. | 96/112 |
| 6,904,815 B2 | 6/2005 | Widmer | |
| 2002/0020232 A1* | 2/2002 | Yamagishi et al. ...... | 73/863.11 |
| 2004/0074319 A1* | 4/2004 | Silvis et al. ............. | 73/864.73 |

* cited by examiner

*Primary Examiner*—Robert Raevis
(74) *Attorney, Agent, or Firm*—Nixon & Vanderhye, PC

(57) ABSTRACT

A heated sampling hose assembly includes a sampling hose having an inlet and an outlet for passage of a sample gas. An outer sleeve surrounds the sampling hose with an annular purge gas passage radially therebetween. The outer sleeve is closed at opposite ends by first and second fittings having a purge gas inlet and purge gas outlet, respectively, and a heater is arranged to heat the purge gas in the annular purge gas passage to a temperature of the sample gas.

19 Claims, 1 Drawing Sheet

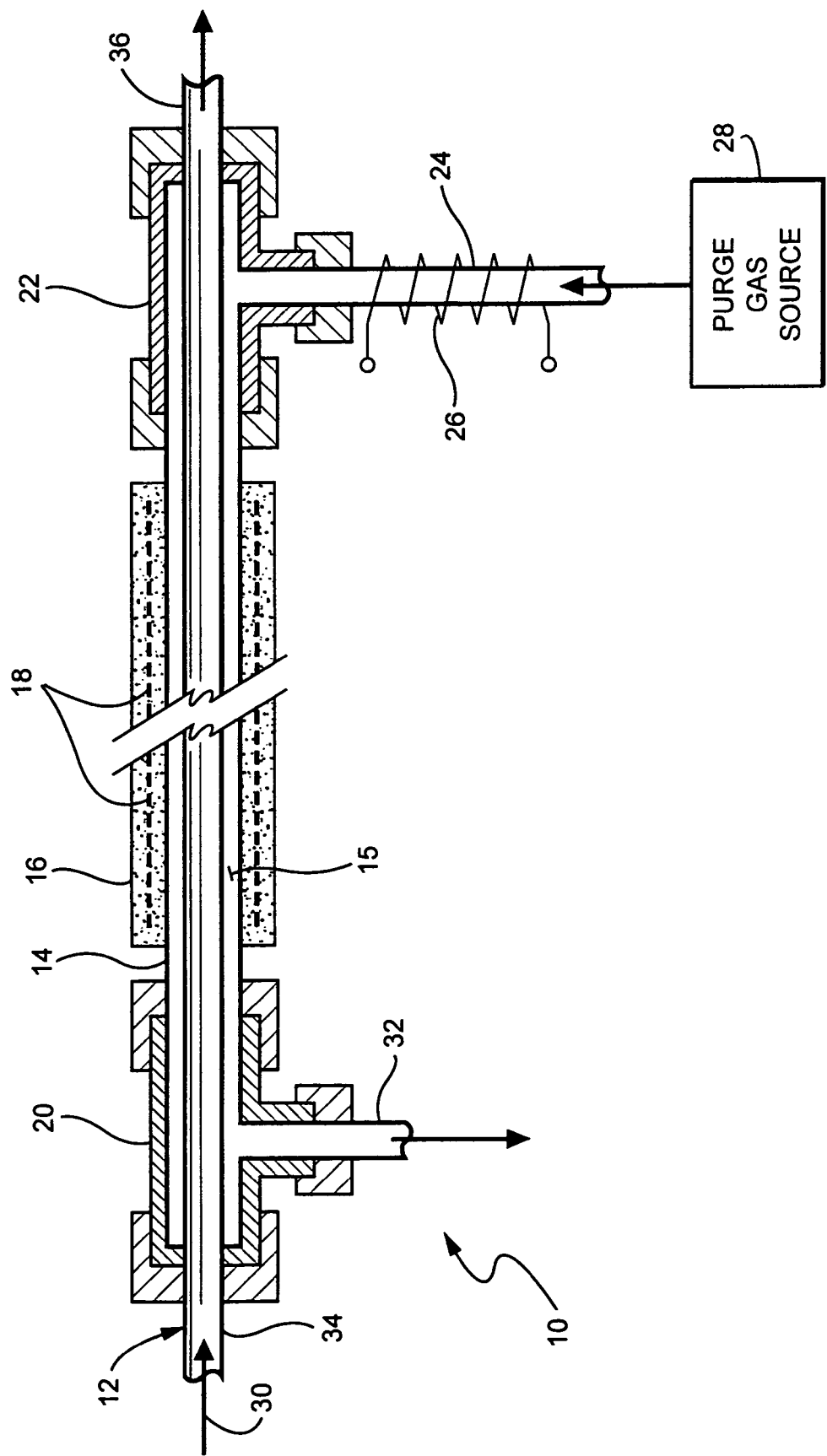

HEATED SAMPLING HOSE ASSEMBLY AND RELATED METHOD

BACKGROUND OF THE INVENTION

This invention relates to exhaust gas sampling and, specifically, to a sampling hose assembly construction that reduces or eliminates sample gas bias due to permeation of gaseous species through the wall of the sampling hose.

Measurements of gaseous pollutants in exhaust stacks of, for example, power generating turbines, are often performed by extraction of exhaust gas through long sampling lines. To avoid condensation of moisture contained in the sample gas and losses of minor exhaust species, these sampling lines are typically heated to high temperatures, ranging from 250 to 350 degrees Fahrenheit.

It has been long known in the stack testing industry, however, that heated lines with fluorocarbon (usually Teflon®) cores often exhibit positive carbon monoxide bias when heated to temperatures in excess of 250° F. In other words, when sampling a known gas, the CO concentration measured at the outlet of the heated line is higher than the CO concentration at the inlet of the heated line. For example, when sampling high purity nitrogen with zero expected CO concentration, the indicated CO concentration can range from 0 to 10 parts per million (ppm), depending on line characteristics (length, diameter, temperature, type of Teflon® material used, wall thickness, etc.).

With increasing demands for accuracy of pollutant measurements, these biases introduced by heated lines quickly become intolerable, especially for measurements of low-level pollutant sources such as gas turbines. The search continues to eliminate or at least significantly reduce heated line bias. To this end, various designs of heated lines and different materials of construction have been proposed. For example, a typical design for a heated sampling line assembly includes a single-wall sampling core (often made of Teflon®), embedded or wrapped in a heating element and surrounded by one or more layers of insulating material such as fiberglass reinforced by organic binders, e.g., phenol-formaldehyde resins. One disadvantage of this traditional design is a potential for exhibiting the above-mentioned "positive bias" by the chemical species diffusing from outside of the sampling line to the inside of the sampling line and into the stream being sampled. In fact, some experimental studies suggest that the source of positive CO bias is carbon monoxide emitted by heat insulating materials at high temperature. This emitted CO diffuses from the outside of the Teflon® core to the inside of the core, increasing the concentration of CO in the sampled stream. The process is facilitated by significant increase of gas diffusivity through Teflon® material at elevated temperatures. The same process of gas diffusion through the walls of a Teflon® sampling core can lead to positively biased concentrations of other important pollutants, such as formaldehyde (albeit at lower concentrations). These situations occur when concentration of the chemical species is higher outside of the sampling core than inside the sampled stream.

Another disadvantage of these traditional sampling line assemblies is the possibility of species diffusion from the stream being sampled and accumulation on the outside of the sampling core, when concentration of the chemical species is higher in the sampled stream than outside of the sampling core. This accumulated chemical species can subsequently be released back into the sampling stream when the concentration in the sampled stream becomes lower than concentration outside of the sample core, i.e., when the chemical species concentration gradient is reversed.

Another design for an improved heated hose bundle includes using a double-wall Teflon® sampling line or tube. This approach essentially includes passing a first Teflon® line of a smaller outside diameter (e.g., ⅜" OD) through a second and larger (e.g., ½" OD) Teflon® line, embedded or wrapped in a heating element and surrounded by insulating materials. Aside from the intended effect of enabling a change of the inner Teflon® core if it becomes contaminated by the exhaust components (such as particulate matter or salt deposits), this design also somewhat reduces the CO bias due to the double Teflon® wall that CO has to permeate before entering the sample stream, but is subject to the diffusion problem mentioned above.

Another possible solution to the problem of positive bias due to diffusion of chemical species from the outside of the sample line into the sample stream includes use of substantially impermeable material such as stainless steel. However, chemical reactivity of stainless steel makes it unsuitable for measurements of certain chemical compounds. Alternative metals or alloys such as Inconel® or Hastealloy® usually have prohibitively high costs, while still not completely eliminating the problem of surface reactivity. Stainless steel tubing can be suitable for particular permanent sampling installations; however, to maintain line flexibility for mobile stack testing applications, the line must be constructed from corrugated stainless steel tubing. If corrugated steel tubing is used for construction of the sample core itself, it introduces significant increase of the inner surface area in contact with the sample stream, which might be detrimental for some trace gas species due to adsorption and/or heterogeneous reaction with the metal surface. Furthermore, a corrugated wall will result in a large number of pockets of essentially stagnant gas in the corrugation folds, significantly increasing sampling system response time. Increase of response time may be critical in applications such as measurements at transient combustion conditions.

These problems can be overcome by using the combination of an outer shell made of corrugated stainless steel and sample core made of Teflon®. Indeed, such a combination would virtually eliminate the positive bias by completely preventing gas diffusion from outside the metal core into the sample stream. However, the sampling hose or tube of this construction would be costly and heavy, making it less suitable for mobile stack testing applications, where cost and weight are two major factors affecting choice of the heated sample hose. Furthermore, due to significant space volume and high surface area between the inner Teflon® and outer corrugated stainless steel cores, such construction will be especially prone to accumulation of permeated gas species between the two cores and the possibility of release of these accumulated species back into the sampled stream when the concentration gradient is reversed, such as during transient or multi-point stack testing.

A further disadvantage of prior heated sampling hose designs is a possible trapping and subsequent release of gases when the sampling lines are applied intermittently for tests at sources with high pollutant concentrations and at sources with low pollutant concentrations (for example, CO and aldehydes). During sampling at sources with high pollutant concentrations, CO and aldehydes would diffuse out of the sample stream through the Teflon® wall and accumulate in the heated line assembly outside the Teflon® sampling hose. These gas species would be trapped there when the heated sampling hose is cooled down at the end of the test and Teflon® gas permeability drops. If later this heated sampling hose is used at a relatively "clean" source with low CO and aldehyde concentrations, the compounds previously trapped would be released when the sampling hose is re-heated, and would tend to diffuse from the outside of the sampling hose into the sample stream due to concentration gradient. This would result in positive measurement bias at the low-level source due to previous exposure to the high-level source. Similar effects could occur when measurements are performed during transient regimes of a combustion source, biasing high-level measurements low and, conversely, biasing low-level measurements high.

BRIEF DESCRIPTION OF THE INVENTION

The proposed invention is a method of reducing the heated sampling hose bias in an exhaust gas sampling hose assembly by purging the space, i.e., the radial gap, between the double walls of the heated sampling hose with a gas essentially free of impurities, such as zero grade nitrogen or air. The source of such a gas can be a compressed gas cylinder, zero-air generator, filtered compressed air, or other sources known in the art. The description of the invention herein focuses on reduction of a positive carbon monoxide bias due to outgassing of CO from heat insulation materials at elevated temperatures and diffusion of this CO into the sample stream. However, it should be obvious that the present invention will in a similar manner reduce positive bias of any chemical species originating outside of the sampling core or hose by reducing diffusion of these species into the sample stream. The CO that is emitted by the heat insulation material diffuses through the wall of the outer line, and is swept away by the purge gas before it can penetrate through the wall of the inner Teflon® tube into the sample stream. It is expected that a counter-flow configuration will have the highest efficiency for minimizing positive CO bias. In order to eliminate moisture condensation and other species losses inside the inner Teflon® line, the purge gas is preheated to a temperature essentially equal to the operating temperature of the heated hose bundle.

Accordingly, in one aspect, the invention relates to a heated sampling hose assembly comprising a sampling hose having an inlet and an outlet for passage of a sample gas; an outer sleeve surrounding the sampling hose with an annular purge gas passage radially therebetween, the sleeve closed at opposite ends by first and second fittings having a purge gas inlet and purge gas outlet, respectively; and a heater arranged to heat purge gas in the annular purge gas passage to a temperature of the sample gas.

In another aspect, the invention relates to a heated sampling hose assembly comprising a sampling hose having an inlet and an outlet; an outer sleeve surrounding the sampling hose with an annular purge gas passage radially therebetween, the sleeve closed at opposite ends by first and second fittings having a purge gas inlet and purge gas outlet, respectively; a first heater surrounding a portion of the outer sleeve and a second heater upstream of the first fitting for heating the purge gas.

In still another aspect, the invention relates to a method of improving measurement accuracy of a sampling hose assembly by reducing sampling bias associated with permeation of chemical species of interest through a sampling hose wall comprising (a) surrounding the sampling hose with an outer sleeve establishing a radial purge passage between the sampling hose and the outer sleeve; (b) providing a source of purge gas substantially free of the chemical species of interest; (c) heating the sampling hose; and (d) passing the purge gas through the radial purge passage while passing a sample gas through the sampling hose.

The invention will now be described in detail in connection with the drawing FIGURE identified below.

BRIEF DESCRIPTION OF THE DRAWINGS

The single drawing FIGURE is a schematic diagram of a sampling hose in accordance with an exemplary embodiment of the invention.

DETAILED DESCRIPTION OF THE INVENTION

With reference to the FIGURE, an elongated sampling core or hose assembly 10 includes a radially inner sampling tube or hose 12 surrounded by an outer shell or sleeve 14. Both the sampling hose 12 and outer shell or sleeve 14 are preferably made of a suitable fluorocarbon polymer material such as polytetrafluoroethylene (e.g., Teflon®). Dimensions suitable for stack sampling applications include a sampling core 10 of ⅜" OD with 0.062" wall thickness, while the outer shell 12 can be constructed of either ⅝" or ½" OD Teflon® tubing with wall thickness of at least 0.035". The thicker wall of the outer shell or sleeve 12 will add primary application to field stack testing.

The radial gap 15 between sampling hose 12 and outer sleeve 14 must be sufficiently large to allow purge gas to flow through the gap with minimal pressure drop, while narrow enough to provide for substantial linear velocity of the purge gas and short residence time of the purge gas inside the outer sleeve. Short residence time will allow efficient sweeping of contaminant species, such as CO that is emitted from insulating material outside the sleeve 12, as described below, before it can diffuse through the wall of the sampling hose 12 into the exhaust gas or other stream being sampled.

The outer sleeve 14 is further surrounded by heat insulation layer or sleeve 16 with an embedded heater 18 made up of conventional heating elements. The length of the outer sleeve 14 must exceed the length of insulation layer 16 to allow for installation of end fittings 20 and 22. Fittings 20 and 22 can be constructed from conventional Swagelok® parts or have any other suitable construction that will allow two separate gas paths, one for the sample flow and another for the purge flow. Various constructions of fittings 20 and 22 will be obvious to those skilled in the art. In the exemplary embodiment of FIG. 1, the sampling hose length exceeds that of the outer shell by approximately 6-8" to accommodate the Swagelok® tube end fittings 20, 22. Fittings 20 and 22 can be externally heated or thermally insulated to avoid cold spots in the sample flow and subsequent moisture condensation and/or gaseous species losses.

Purge flow inlet 24 may be provided with a heater 26 that serves to preheat the purge gas from source 28 to the temperature of the sample gas stream 30 and thus avoid cold spot formation. Purge gas flows out of the system through the purge outlet 32. The purge gas preferably moves in a counterflow direction with respect to the sampling gas stream 30 that is delivered via inlet 34 and through the sampling outlet 36 to gas analysis equipment (not shown).

In addition to removing the contaminant species such as carbon monoxide and aldehydes from outside of the sampling core 10 and preventing their diffusion into the sample stream 30, the purge gas flow enhances heat transfer from the outer shell 14 to the sampling hose 12. Enhanced heat transfer offers further advantages such as shorter heat-up time and more even temperature distribution inside the heated core, substantially reducing the possibility of formation of hot spots and subsequent damage to the core. An even further advantage of the present invention includes reduced contact between the walls of the sampling hose 12 and elements of the heater 18. This feature helps preserve the integrity of the sampling hose 12 in case of temperature control circuitry malfunction, such as in the case of overheating caused by failed solid-state relay, when heated elements could reach temperatures in excess of 500° F. (above Teflon® softening temperatures).

In the first exemplary embodiment of the present invention, a combination of Teflon® outer sleeve/Teflon® sampling hose with purge gas between the two, does not completely eliminate diffusion of gaseous species into and out of the sample stream. However, as shown by experimental investigation, the present invention does reduce the bias caused by diffusion through Teflon® wall to essentially negligible levels. Furthermore, the present invention offers weight characteristics similar to standard heated hoses used in the field and in case of sample hose failure such as structural damage or contamination by conditions, provides a low-cost repair alternative to replacement of the whole heated sampling hose assembly. The present invention also provides the ability to control the amount of residual positive bias when sampling low-level sources, and negative bias when sampling high-level sources to the extent desired by adjusting the flow rate of the purge gas.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A heated sampling hose assembly comprising a sampling hose having an inlet and an outlet for passage of a sample gas; an outer sleeve surrounding said sampling hose with an annular purge gas passage radially therebetween, said sleeve closed at opposite ends by first and second fittings having a purge gas inlet and purge gas outlet, respectively; and a heater arranged to heat purge gas in said annular purge gas passage to a temperature of said sample gas, wherein materials for said sampling hose and said outer sleeve and the flow of the said purge gas are chosen so as to reduce transport of one or more gaseous species of interest across the walls of said sampling hose.

2. The heated sampling hose assembly of claim 1 wherein said heater comprises heating elements embedded in an insulating sleeve surrounding at least a portion of said outer sleeve.

3. The heated sampling hose assembly of claim 2 wherein said insulating sleeve extends substantially an entire axial distance between said first and second fittings.

4. The heated sampling hose assembly of claim 1 wherein said purge gas inlet and said purge gas outlet extend substantially perpendicularly to said as sampling hose.

5. The heated sampling hose assembly of claim 1 and further comprising a second heater arranged to heat purge gas upstream of said first fitting.

6. The heated sampling hose assembly of claim 1 wherein said purge gas comprises compressed nitrogen.

7. The heated sampling hose assembly of claim 1 wherein said purge gas comprises compressed air.

8. The heated sampling hose assembly of claim 1 and further comprising a pressurized source of said purge gas.

9. The heated sampling hose assembly of claim 8 wherein said source comprises a compressed gas cylinder.

10. The heated sampling hose assembly of claim 2 wherein said insulating sleeve is comprised of phenolformaldehyde resins.

11. The heated sampling hose assembly of claim 1 wherein said outer sleeve is comprised of polytetrafluoroethylene.

12. The heated sampling hose assembly of claim 1 wherein said sampling hose is comprised of polytetrafluoroethylene.

13. A method of improving measurement accuracy of a sampling hose assembly by reducing sampling bias associated with permeation of chemical species of interest through a sampling hose into a sample gas comprising:
   (a) surrounding the sampling hose with an outer sleeve establishing a radial purge passage between the sampling hose and the outer sleeve;
   (b) providing a source of purge gas substantially free of the chemical species of interest;
   (c) heating the sampling hose; and
   (d) passing said purge gas through said radial purge passage while passing the sample gas through the sampling hose, wherein materials for said sampling hose and said outer sleeve and the flow of the said purge gas are chosen so as to reduce transport of one or more gaseous species of interest across the walls of said sampling hose.

14. The method of claim 13 wherein said chemical species of interest is carbon monoxide.

15. The method of claim 13 wherein said chemical species of interest is an aldehyde.

16. The method of claim 13 wherein, during step (c), said sampling hose is heated to a temperature of at least 250° F.

17. The method of claim 13 wherein said outer sleeve is composed of a fluoropolymer.

18. The method of claim 13 wherein said sampling hose is composed of a fluoropolymer.

19. A method of improving measurement accuracy of a sampling hose assembly by reducing sampling bias associated with permeation of chemical species of interest through a sampling hose into a sample gas comprising:
   (a) surrounding the sampling hose with an outer sleeve establishing a radial purge passage between the sampling hose and the outer sleeve;
   (b) providing a source of purge gas substantially free of the chemical species of interest;
   (c) heating the sampling hose; and
   (d) passing said purge gas through said radial purge passage while passing the sample gas through the sampling hose, and wherein the sample gas comprises exhaust gas from a powergeneration turbine.

* * * * *